United States Patent [19]

Gruenfeld

[11] 4,173,633
[45] Nov. 6, 1979

[54] INDENO AND NAPHTH[1,2-d]AZEPINES

[75] Inventor: Norbert Gruenfeld, White Plains, N.Y.

[73] Assignee: Ciba-Geigy Corporation, Ardsley, N.Y.

[21] Appl. No.: 856,703

[22] Filed: Dec. 2, 1977

[51] Int. Cl.$^2$ .................. C07D 403/06; A61K 31/55; C07D 223/14

[52] U.S. Cl. .................. 424/244; 260/239.3 T; 544/60; 544/111; 544/359; 546/200; 424/248.54; 424/248.56; 424/246; 424/250; 424/267; 424/274; 260/239 BB; 260/326.81

[58] Field of Search .................. 260/239.3 T; 424/244, 424/248.54, 248.56, 246, 250, 267, 274

[56] References Cited
PUBLICATIONS

"Chemical Abstracts", vol. 81 (1974), Item 3250c, abstracting Boyakhchyan et al., in Arm. Khim. Zh., (1973), vol. 26, No. 12, pp. 1026–1029.

*Primary Examiner*—John M. Ford
*Assistant Examiner*—Robert T. Bond
*Attorney, Agent, or Firm*—Theodore O. Groeger

[57] ABSTRACT

Hydrogenated 1-aminoalkyl-indeno- or naphth[1,2-d]-azepines, e.g. those of the formula

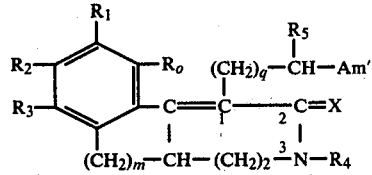

Am′=NH$_2$, (alkyl, alkenyl, alkynyl, hydroxyalkyl, cycloalkyl, or benzyl)amino, its N-lower alkyl derivatives; alkyleneimino morpholino or piperazino;
R$_{o-3}$=H, OH, alkyl, alkoxy, halo or CF$_3$;
R$_{4,5}$=H or alkyl;
X=H$_2$ or O;
m=1 or 2;
q=0 or 1;

and salts thereof are potassium-sparing diuretic agents.

9 Claims, No Drawings

INDENO AND NAPHTH[1,2-d]AZEPINES

SUMMARY OF THE INVENTION

The present invention concerns and has for its object the provision of new 1-aminoalkyl-2,3,4,5,5a,6-hexahydro-indeno- or 3,4,5,5a,6,7-hexahydro-2H-naphth[1,2-d]azepines, preferably of those corresponding to Formula I

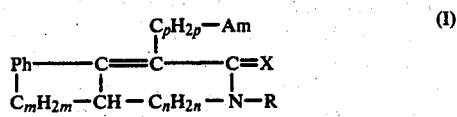

wherein Ph is unsubstituted 1,2-phenylene, or 1,2-phenylene substituted by up to 3 members selected from lower alkyl, hydroxy, mercapto, lower alkoxy, lower alkylthio, lower alkenyloxy, halogeno and trifluoromethyl; $C_mH_{2m}$ is lower alkylene separating the adjacent atoms by one or two carbon atoms; $C_nH_{2n}$ is lower alkylene separating the adjacent atoms by two carbon atoms; p is an integer from 1 to 7; Am is amino, simple or mixed, mono- or di-lower (alkyl, alkenyl, alkynyl, hydroxyalkyl, 3 to 7 ring-membered cycloalkyl or H-Ph-alkyl)amino; mono- or bicyclic, 5 to 7 ring-membered lower alkyleneimino, or lower mono(oxa, thia or aza)-alkyleneimino; X represents two hydrogens or oxo and R is hydrogen, lower alkyl or hydroxyalkyl; a lower alkanoyl- or 1,11b-dihydro-derivative, or a therapeutically useful acid addition salt thereof; as well as of corresponding pharmaceutical compositions and of methods for the preparation and application of these products, which are useful diuretic agents.

DESCRIPTION OF THE PREFERRED EMBODIMENTS

The 1,2-phenylene radical Ph is preferably 1,2-phenylene substituted by up to three, especially one or two, of the same or different members selected from the group consisting of lower alkyl, e.g. methyl, ethyl, n- or i-propyl or -butyl; free, etherified or esterified hydroxy or mercapto, such as lower alkoxy, e.g. methoxy, ethoxy, n- or i-propoxy or -butoxy; lower alkenyloxy, e.g. allyloxy or 2-propenyloxy; lower alkylthio, e.g. methylthio or ethylthio; halogeno, e.g. fluoro, chloro or bromo; or trifluoromethyl. Preferred Ph-radicals are 1,2-phenylene, (lower alkyl)-1,2-phenylene, (hydroxy)-1,2-phenylene, mono or di-(lower alkoxy)-1,2-phenylene, (halogeno)-1,2-phenylene or (trifluoromethyl)-1,2-phenylene.

The term "lower", referred to above and hereinafter in connection with organic radicals or compounds respectively, defines such with up to 7, preferably up to 4, carbon atoms.

The radicals $C_mH_{2m}$ and $C_nH_{2n}$ preferably represent ethylene, but may also stand for 1,2-propylene, 1,2- or 2,3-butylene and $C_mH_{2m}$ may also represent methylene.

The lower alkylene radical $C_pH_{2p}$ is preferably ethylene or 1,2-propylene, but also represents methylene, 1,3-propylene, 1,2- 1,3- or 1,4-butylene, 1,2- 1,3- or 1,4-pentylene, -hexylene or -heptylene.

The open or cyclic amino group Am is exemplified by amino, lower (alkyl, alkenyl, alkynyl or hydroxyalkyl)amino, e.g. (methyl, ethyl, n- or i-propyl, -butyl, -pentyl, -hexyl or -heptyl; allyl, 2- or 3-butenyl; propargyl, 2- or 3-butynyl; 2-hydroxyethyl, 2- or 3-hydroxypropyl)amino; (3 to 7 ring-membered cycloalkyl or HPh-lower alkyl)-amino, e.g. (cyclopentyl, cyclohexyl; benzyl or phenethyl)amino; or the N-lower alkyl-derivatives of said sec. amino groups, e.g. the N-(methyl, ethyl, n- or i-propyl, -butyl, -pentyl, -hexyl or -heptyl)- derivatives thereof; 5 to 7 ring-membered mono- or bicyclic lower alkeleneimino, e.g. pyrrolidino, piperidino, (1,4-, 1,5-, 1,6-, 2,5-, 2,6-, or 1,7-hexylene or -heptylene)imino; 2- or 3-azabicyclo [3.2.2]nonyl or [4.3.1]decyl; or lower mono-oxa, thia or azaalkyleneimino, e.g. morpholino, thiamorpholino, piperazino or N-(lower alkyl or hydroxyalkyl)-piperazino, e.g. N-(methyl, ethyl or 2-hydroxyethyl)-piperazino.

The radical X is preferably oxo and R advantageously hydrogen, but also lower alkyl or hydroxyalkyl, preferably methyl ethyl, hydroxymethyl or 2-hydroxyethyl.

The lower alkanoyl derivatives of said compounds of Formula I are preferably those containing alkanoyl attached to a primary or secondary amino group Am, and/or those wherein $X=H_2$ and $R=H$; e.g. the acetyl, propionyl or pivaloyl derivatives.

Salts of the compounds of Formula I are preferably addition salts of the therapeutically useful inorganic or organic acids listed below.

The compounds of the invention exhibit valuable pharmacological properties. Primarily they show diuretic, natri- and chloroiuretic activity with rapid onset of action, high urine but low potassium excretion levels. This can be demonstrated in animal tests using, for example, mammals, e.g. rats or dogs, as test objects. Such tests are performed, for example, by administering the compounds of the invention within a gelatin capsule to dogs, or in the form of aqueous solutions or starchy suspensions by stomach tube to rats, in an oral dosage range between about 0.5 and 100 mg/kg/day, preferably between about 1 and 50 mg/kg/day, advantageously between about 5 and 25 mg/kg/day. Simultaneously the test animals may receive various salt loads enterally or parenterally, for example various amounts of subcutaneously applied 0.9% saline, e.g. 100 ml thereof per medium-sized dog (beagle). Urine is then collected, e.g. at 2 hour intervals, with or without catheterization, and its volume, sodium, potassium and chloride content estimated and compared with that of the same untreated or saline-treated animals. Besides the anti-edematous utility, the compounds of the invention can also be used as intermediates in the preparation of other valuable products, primarily or pharmacologically active compounds or compositions, e.g. as components of antihypertensive agents.

Preferred and highly diuretic are those compounds of Formula I in which Ph is 1,2-phenylene, (lower alkyl)-1,2-phenylene, (hydroxy)-1,2-phenylene, mono or di-(lower alkoxy)-1,2-phenylene, (halogeno)-1,2-phenylene or (trifluoromethyl)-1,2-phenylene; $C_mH_{2m}$ is methylene, ethylene or 1,2-propylene; $C_nH_{2n}$ is ethylene or 1,2-propylene, p is an integer from 1 to 7, Am is amino, lower (alkyl, alkenyl, alkynyl, hydroxy alkyl, 5 or 6 ring-membered cycloalkyl or phenyl-lower alkyl)amino, the N-lower alkyl-derivatives of said sec. amino groups; 5 to 7 ring-membered lower alkyleneimino, morpholino, thiamorpholino, piperazino or N-(lower alkyl or hydroxyalkyl)-piperazino; X represents two hydrogens or oxo and R is hydrogen, lower alkyl or hydroxyalkyl; the lower alkanoyl derivatives of said compounds wherein Am is prim. or sec. amino or both X and R are hydrogen; the 1,11b-dihydro-derivatives or a therapeutically useful acid addition salt thereof.

Especially valuable and suitable for said utility are compounds of Formula II

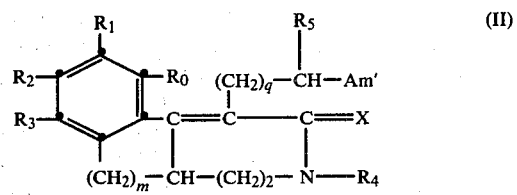

wherein each of $R_0$, $R_1$, $R_2$ and $R_3$ is hydrogen, or one thereof is alkyl with up to 4 carbon atoms, hydroxy, fluoro, chloro, bromo or trifluoromethyl; or one or two thereof are alkoxy with up to 4 carbon atoms and the others are hydrogen, Am' is amino, lower (alkyl, alkenyl, alkynyl, hydroxyalkyl, 5 or 6 ring-membered cycloalkyl or benzyl)amino, the N-lower alkyl derivatives of said sec. amino groups, 5 to 7 ring-membered lower alkyleneimino, morpholino, thiamorpholino, piperazino or N-lower alkyl-piperazino; X represents two hydrogens or oxo; each of $R_4$ and $R_5$ is hydrogen or alkyl with up to 4 carbon atoms; m is the integer 1 or 2 and q is 0 or 1; or a therapeutically useful acid addition salt thereof.

More preferred are compounds of Formula II, wherein each of $R_0$, $R_1$, $R_2$ and $R_3$ is hydrogen, or up to two of $R_0$, $R_1$, $R_2$ and $R_3$ are methoxy, or one thereof is methyl, hydroxy, fluoro, chloro or trifluoromethyl and the others are hydrogen; Am' is amino (methyl, ethyl, n- or i-propyl, allyl, propargyl, 2-hydroxyethyl, cyclopentyl, cyclohexyl or benzyl)amino, or the N-(methyl, ethyl, n- or i-propyl, -butyl, -pentyl, -hexyl or -heptyl)-derivatives of said sec. amino groups, pyrrolidino, piperidino, morpholino or N-methylpiperazino, X is oxo; each of $R_4$ and $R_5$ is hydrogen or methyl; m is 2 and q is one; or a therapeutically useful acid addition salt thereof.

Outstanding are compounds of Formula II, wherein each of $R_0$, $R_1$, $R_2$ and $R_3$ is hydrogen, or up to two thereof are methoxy and the others are hydrogen; $R_4$ is hydrogen; $R_5$ is methyl; Am' is (methyl, ethyl, n- or i-propyl, allyl or propargyl)amino, or the N-(methyl, ethyl, i-propyl or n-butyl)-derivative thereof, pyrrolidino, piperidino or morpholino; X is oxo, m is two and q is one; or a therapeutically useful acid addition salt thereof, which, when given to rats or dogs at oral doses as low as 1.25 mg/kg/day, exhibit marked diuretic, natri- and chloriuretic effects with little effect on potassium excretion.

The compounds of the invention are prepared according to methods in themselves known. Advantageously, they are obtained by reducing Schiff's bases or oximes obtained from compounds of Formula III

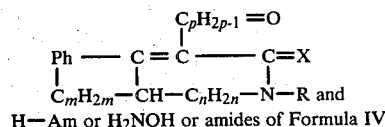

H—Am or $H_2NOH$ or amides of Formula IV

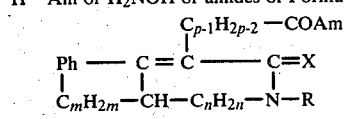

and, if desired, converting any resulting compound into another compound of the invention.

Said reduction is carried out according to known methods, for example with the use of hydrogen in the presence of catalysts e.g. platinum or nickel catalysts, or with nascent hydrogen, e.g. generated electrolytically, advantageously in case of said Schiff's bases or oximes. Also reducing agents are useful for both of said carbonyl- or acid-derived starting materials, preferably simple or complex light metal hydrides, such as aluminum- or borohydrides, e.g. alane, boranes or sodium cyanoborohydride, in case a carbonyl group in 2-position should be preserved; or stronger reducing agents converting X═O to X═H2 also, such as alkali metal aluminum hydrides, e.g. lithium aluminum hydride.

The starting material is new and compounds of Formula III are preferably prepared by adding corresponding 3,3a,4,5-tetrahydro-2H-benz[g]indoles [JACS 93, 3834 (1971)] to butenolides, preferably α-angelicalactone, either in the absence or presence of diluents, such as hydrocarbons or esters, e.g. toluene, xylene or ethyl acetate, advantageously at elevated temperatures, e.g. between 80° and 140°. Said amides of Formula IV are advantageously prepared from those of Formula I, especially Formula II wherein $R_5$ is alkyl, q is 1 and Am is monoalkylamino, by treatment with butyl lithium, followed by reaction with carbon dioxide and amidizing the resulting acid with HAm and 1,1'-carbonyldiimidazole.

Another process for preparing the compounds of the invention consists in condensing reactive esters of Formula V

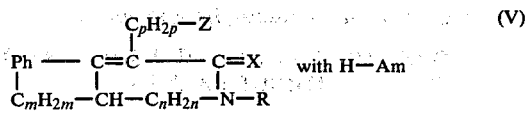

wherein Z is a reactively esterified hydroxy group, for example, such esterified by a strong inorganic or organic acid, above all a hydrohalic acid, e.g. hydrochloric, hydrobromic or hydriodic acid; sulfuric or an aromatic sulfonic acid, e.g. p-toluene or m-bromobenzene sulfonic acid. Said condensation is preferably carried out in the presence or absence of a basic agent, such as an alkali or alkaline earth metal hydroxide, carbonate or bicarbonate, e.g. sodium, potassium or calcium hydroxide or carbonate; alkali metal hydrides, lower alkoxides or alkanoates, e.g. sodium hydride, methylate or acetate, as well as organic tertiary nitrogen bases, such as tri-lower alkylamines or pyridines, e.g. triethylamine or lutidine.

The starting material of Formula V can be prepared by reducing the compounds of Formula III to the corresponding alcohols, e.g. with sodium borohydride, and reactively esterifying them with said inorganic or organic acids, or reactive derivatives thereof, e.g. phosphorus trihalides or sulfonyl halides. Variously compounds of Formula V, wherein Z is hydrogen and p is 1, can be lithiated, e.g. with n-butyl lithium, and reacted with lower alkyl disulfides, to yield compounds V with Z being lower alkylthio. These, in turn, can be converted into those with Z being halogen, by cleaving them with sulfuryl halides; e.g. sulfuryl chloride.

The compounds of the invention thus obtained can be converted into each other according to conventional methods. For example, resulting phenolethers may be hydrolyzed with hydrobromic acid or boron tribromide, or prim. or sec. amines reacted with reactive esters of the respective alcohols, preferably derived from hydrohalic, aliphatic or aromatic sulfonic acids, e.g. lower alkyl sulfonates, e.g. the mesylate or tosylate, or with corresponding aldehydes or ketones and reducing agents, e.g. formic acid or sodium cyanoborohydride, in order to obtain sec. or tert. amines, respectively. Acyl-derivatives of prim. or sec. amines are obtained by conventional acylation with reactive acid derivatives, e.g. anhydrides or halides. Resulting acyl derivatives, or compounds of Formula I with X=O, can be reduced as shown for the amides of Formula IV, e.g. mildy with said simple hydrides, such as alane or boranes in order to retain X=O, or with stronger complex metal hydrides, e.g. lithium aluminum hydride, in order to obtain compounds with X=H$_2$. Said 1,11b-dihydro derivatives of the compounds of Formula I are obtained by catalytical hydrogenation, e.g. in the presence of platinum catalysts and lower alkanoic acids, such as acetic acid.

Finally, a resulting base can be converted into a corresponding acid addition salt, preferably with the use of a therapeutically acceptable acid or anion exchange preparation; or resulting salts can be converted into the corresponding free bases, for example, with the use of a base, such as a metal hydroxide, basic salt, ammonia, amine or cation exchange preparation, e.g. an alkali metal hydroxide or carbonate. Said acid addition salts are preferably such of therapeutically useful inorganic acids, such as strong metalloidic acids, for example, hydrohalic, e.g. hydrochloric or hydrobromic acid; sulfuric, phosphoric, nitric or perchloric acid; aliphatic or aromatic carboxylic or sulfonic acids, e.g. formic, acetic, propionic, succinic, glycollic, lactic, malic, tartaric, citric, ascorbic, maleic, hydroxymaleic, pyruvic, phenylacetic, benzoic, 4-aminobenzoic, anthranilic, 4-hydroxybenzoic, salicylic, embonic, nicotinic; methanesulfonic, ethanesulfonic, hydroxyethanesulfonic, ethylenesulfonic, halogen-benzenesulfonic, toluenesulfonic, naphthalenesulfonic, sulfanilic or cyclohexylsulfamic acid.

These or other salts, for example, the picrates or tetrafluoroborates, can also be used for purification of the bases obtained; the bases are converted into salts, the salts are separated and the bases are liberated from the salts. In view of the close relationship between the free compounds and the compounds in the form of their salts, whenever a compound is referred to in this context, a corresponding salt is also intended, provided such is possible or appropriate under the circumstances. Resulting mixtures of isomers, e.g. diastereo or optical isomers, can be separated into the single isomers by methods in themselves known, e.g. by fractional distillation, crystallization and/or chromatography, or separation of diastereomeric salts. As is obvious from Formula II, both carbons in the CHAm'-moiety (R$_5 \neq$ hydrogen) and at position 5a of the ring-system represent asymmetric carbon atoms, yielding RR-racemates with both of said hydrogen atoms in cis-position (Formula in Example 1), or RS-racemates with these hydrogen atoms trans to each other.

The invention further includes any variant of the present process in which an intermediate product obtainable at any stage of the process is used as starting material and any remaining steps are carried out, or the process is discontinued at any stage thereof, or in which the starting materials are formed under the reaction conditions, or in which the reaction components are used in the form of their salts. Mainly those starting materials should be used in the reactions of the invention that lead to the formation of those compounds indicated above as being especially valuable.

The above reactions are carried out according to standard methods, in the presence or absence of diluents, preferably such as are inert to the reagents and are solvents thereof, of catalysts, condensing or neutralizing agents and/or inert atmospheres, at low temperatures, room temperature or advantageously elevated temperatures, at atmospheric or superatmospheric pressure.

The pharmacologically active compounds of the invention are useful in the manufacture of pharmaceutical compositions containing an effective amount thereof in conjunction or admixture with excipients suitable for either enteral or parenteral application. Preferred are tablets and gelatin capsules comprising the active ingredient together with (a) diluents, e.g. lactose, dextrose, sucrose, mannitol, sorbitol, cellulose and/or glycine, (b) lubricants, e.g. silica, talcum, stearic acid, its magnesium or calcium salt and/or polyethyleneglycol, for tablets also (c) binders, e.g. magnesium aluminum silicate, starch paste, gelatin, tragacanth, methylcellulose, sodium carboxymethylcellulose and/or polyvinyl-pyrrolidone, if desired, (d) disintegrants, e.g. starches, agar, alginic acid or its sodium salt, enzymes of the binders or effervescent mixtures and/or (e) absorbents, colorants, flavors and sweeteners. Injectable compositions are preferably aqueous isotonic solutions or suspensions, and suppositories are advantageously fatty emulsions or suspensions. They may be sterilized and/or contain adjuvants, such as preserving, stabilizing, wetting or emulsifying agents, solution promotors, salts for regulating the osmotic pressure and/or buffers. They may also contain other therapeutically valuable substances. Said pharmaceutical compositions are prepared according to conventional mixing, granulating or coating methods respectively and contain about 0.1 to 75%, preferably about 1 to 50% of the active ingredient.

The following examples, illustrating the invention, are not to be construed as being limitations thereon. Temperatures are given in degrees Centigrade and all parts wherever given are parts by weight. If not mentioned otherwise, all evaporations are performed under reduced pressure, e.g. between about 15 and 100 mmHg.

EXAMPLE 1

The solution of 42 g of 1-(2-oxopropyl)-3,4,5,5a,6,7-hexahydro-9-methoxy-2H-naphth[1,2-d]azepin-2-one, 71.4 ml of isopropylamine, 32.5 ml of 5 N methanolic hydrochloric acid and 9.5 g of sodium cyanoborohydride in 730 ml of methanol is refluxed for 2 days. It is cooled, acidified to pH=1 with concentrated hydrochloric acid and evaporated to remove the methanol. The concentrate is diluted with 175 ml of water, the mixture washed three times with diethyl ether and rendered basic to pH=10-11 with 3 N aqueous sodium hydroxide. It is extracted with diethyl ether, and the extract is evaporated. The residue is slurried in ethyl acetate and filtered, to give an impure "slow moving" isomer, melting at 155°-158° [denoted by relative migration in thin layer chromatography; stationary phase is silica gel and moving phase is ethyl acetate-ethanol-aqueous ammonia (90:10:3)]. It is dissolved in 400 ml of acetone and the solution treated with 15 ml of 4.4 N ethanolic hydrochloric acid. The crystalline salt is collected and recrystallized from isopropanol-acetone to give the pure hydrochloride of said slow moving isomer melting at 233°–235°. Reconversion to the free base with ammonia gives the "slow moving" 1-(2-isopropylaminopropyl)-3,4,5,5a,6,7-hexahydro-9-methoxy-2H-naphth[1,2-d]azepin-2-one of the formula

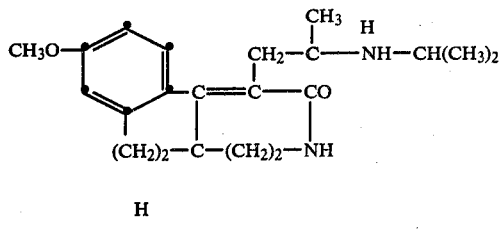

melting at 167°–169°; it is the RR-racemate.

The mother liquor from said ethyl acetate treatment of crude product is evaporated and the residual oil is dissolved in acetone and treated with 9.7 ml of 4.4 N ethanolic hydrochloric acid, to give the "fast moving" isomer's hydrochloride. It crystallizes slowly and is recrystallized from ethanol-acetone, m.p. 238°–240°; it is the RS-racemate.

The starting material is prepared as follows:
13.5 g of 2-dimethylaminomethyl-6-methoxy-1-tetralone hydrochloride (C. A. 41, 6253 g) are dissolved in 200 ml of water and 4 ml of concentrated hydrochloric acid are added, followed by the concentrated aqueous solution of 6.5 g of potassium cyanide, introduced below the surface of the liquid. The mixture is refluxed for one hour, stirred at room temperature overnight and filtered, to yield the 2-cyanomethyl-6-methoxy-1-tetralone melting at 90°–93°. Similarly prepared are the following nitriles: 2-cyanomethyl-1-tetralone, b.p. 125°–30°/0.005 mm Hg; 2-cyanomethyl-6,7-dimethoxy-1-tetralone, m.p. 116°–118°; 2-cyanomethyl-7-methoxy-1-tetralone, m.p. 80°–84°: 2-cyanomethyl-5-methoxy-1-tetralone, m.p. 91°–94°.

The solution of 50 g of 2-cyanomethyl-6-methoxy-1-tetralone in 1000 ml of ethanol is hydrogenated in the presence of 15 g of Raney nickel at atmospheric pressure and room temperature until 2 mole equivalents of hydrogen are consumed. The mixture is filtered, the filtrate evaporated and the crude product dissolved in 500 ml of N hydrochloric acid. The solution is washed with diethyl ether, treated with charcoal, filtered and the filtrate is basified with 3 N aqueous sodium hydroxide. It is extracted with methylene chloride, the extract dried, evaporated, the residue crystallized from petroleum ether and recrystallized from hexane, to yield the 7-methoxy-3,3a,4,5-tetrahydro-2H-benz[g]indole melting at 102°–104°.

Analogously the 3,3a,4,5-tetrahydro-2H-benz[g]indole, I.R.-band at 1620 cm$^{-1}$; its 7,8-dimethoxy-derivative, m.p. 133°–136°; its 8-metoxy-derivative, m.p. 77°–79° and its 6-methoxy-derivative, m.p. 78°–81° are prepared.

19.6 g of commercial α-angelicalactone are added in 4 portions at hourly intervals to the refluxing solution of 20.1 g of 7-methoxy-3,3a,4,5-tetrahydro-2H-benz[g]indole in 150 ml of toluene and reflux is continued overnight. The solution is cooled, leading to crystallization of the 1-(2-oxopropyl)-3,4,5,5a,6,7-hexahydro-9-methoxy-2H-naphth[1,2-d]-azepin-2-one melting at 212°–214°.

Similarly prepared is the 1-(2-oxopropyl)-3,4,5,5a,6,7-hexahydro-2H-naphth[1,2-d]azepin-2-one, m.p. 217°–218°; its 9,10-dimethoxy-derivative; its 10-methoxy-derivative, m.p. 218°–220° and its 8-methoxy-derivative, m.p. 215°–217°.

EXAMPLE 2

The solution of 13.8 g of 1-(2-hydroxyiminopropyl)-3,4,5,5 a,6,7-hexahydro-9-methoxy-2H-naphth[1,2-d]azepin-2-one in 350 ml of ethanol is hydrogenated at atmospheric pressure and room temperature in the presence of 15 g of Raney nickel until the required amount of hydrogen is taken up. The catalyst is filtered off, the filtrate is evaporated to dryness and the residue crystallized from diethyl ether. The residue is dissolved in ethanol, the solution acidified with ethanolic hydrochloric acid, treated with charcoal, filtered and evaporated. The residue is crystallized from acetone, to yield the 1-(2-aminopropyl)-3,4,5,5a,6,7-hexahydro-9-methoxy-2H-naphth[1,2-d]azepin-2-one hydrochloride melting at 240°–242°.

The starting material is prepared as follows: 5.8 g of hydroxylamine hydrochloride are added to the mixture of 15 g of 1-(2-oxopropyl)-3,4,5,5a,6,7-hexahydro-9-methoxy-2H-naphth[1,2-d]-azepin-2-one, 6.2 g of powdered potassium carbonate, 120 ml of methanol and 10 ml of water. It is refluxed for three hours and stirred at room temperature overnight. The suspension is evaporated, the residue is suspended in 200 ml of chloroform-water (3:1) and filtered off, to yield the 1-(2-hydroxyiminopropyl)-3,4,5,5a,6,7-hexahydro-9-methoxy-2H-naphth[1,2-d]azepin-2-one melting at 216°–218°.

EXAMPLE 3

80 ml of 1 M diborane in tetrahydrofuran are added to the suspension of 6.8 g of [9-methoxy-2-oxo-3,4,5,5a,6,7-hexahydro-2H-naphth-[1,2-d]azepin-1-yl]-N-isopropyl-acetamide in 100 ml of tetrahydrofuran while stirring under nitrogen at 0°. After 20 hours 60 ml of 3 N hydrochloric acid are added dropwise and the mixture is refluxed for one hour. The tetrahydrofuran is distilled off under reduced pressure and the remainder is diluted with water. The resulting precipitate is filtered off and re-extracted with hot water. The aqueous filtrate is washed with diethyl ether and basified with 3 N aqueous sodium hydroxide. The suspension is extracted with methylene chloride, the extract dried, evaporated and the residue recrystallized from acetone, to yield the 1-(2-isopropylaminoethyl)-3,4,5,5a,6,7-hexahydro-9-methoxy-2H-naphth[1,2-d]azepin-2-one melting at 147°–149°.

The starting material is prepared as follows: 19.2 ml of tetramethyl-ethylenediamine are added under nitrogen to 53.3 ml of 2.4 M n-butyl lithium in hexane at room temperature and the mixture is allowed to react for 15 minutes. Thereupon the solution of 10.9 g of 1-(2-isopropylaminopropyl)-3,4,5,5a,6,7-hexahydro-9-methoxy-2H-naphth[1,2-d]azepin-2-one in 160 ml of anhydrous tetrahydrofuran is added dropwise. The mixture is refluxed for 30 minutes and subsequently cooled in an ice bath. 120 ml of water are added dropwise and the mixture is stirred with cooling for 30 minutes. The precipitate is collected, washed with water and diethyl ether and dried, to yield the 1-methyl-9-methoxy-3,4,5,5a,6,7-hexahydro-2H-naphth[1,2-d]azepin-2-one melting at 215°–218°.

To the suspension of 10 g thereof in 120 ml of anhydrous tetrahydrofuran 48.7 ml of 2.4 M n-butyl lithium in hexane are added at room temperature and the mixture is stirred at said temperature for 45 minutes. It is transferred by syringe beneath the surface of a slurry of dry ice in diethyl ether and allowed to react overnight. The suspension is extracted with 300 ml of water, the aqueous solution washed with diethyl ether, treated with charcoal and acidified to pH=1 with 6 N hydrochloric acid. The resulting precipitate is collected, washed with diethyl ether and dried. It is purified by dissolving in saturated aqueous sodium bicarbonate, washing the solution with diethyl ether and reprecipitating the product by acidification with 6 N hydrochloric acid, to yield the [9-methoxy-2-oxo-3,4,5,5a,6,7-hexahydro-2H-naphth[1,2-d]azepin-1-yl]-acetic acid melting at 232°–234° with decomposition.

To the suspension of 7.6 g thereof in 120 ml of anhydrous tetrahydrofuran 6.1 g of 1,1′-carbonyldiimidazole are added while stirring under nitrogen at room temperature. The mixture is stirred 15 minutes longer, 10.8 ml of isopropylamine are added dropwise and stirring is continued at room temperature overnight. The precipitate obtained after cooling is collected and washed with diethyl ether, to yield the [9-methoxy-2-oxo-3,4,5,5a,6,7-hexahydro-2H-naphth[1,2-d]azepin-1-yl]-N-isopropylacetamide m.p. 213°–216°. Also prepared are the piperidino and dimethylamino amides melting at 220°–223° and 225°–227° respectively.

EXAMPLE 4

25.7 ml of 1.1 M alane-triethylamine in benzene are added dropwise to the suspension of 7.7 g of [9-methoxy-2-oxo-3, 4,5,5a,6,7-hexahydro-2H-naphth[1,2-d]azepin-1-yl]-acetyl-piperidine in 85 ml of anhydrous tetrahydrofuran at 0°. The mixture is stirred for 3 hours at 0° and at room temperature for one hour. It is cooled, 20 ml of water are added dropwise, followed by 20 ml of 3 N aqueous sodium hydroxide. The resulting mixture is extracted with 400 ml of diethyl ether, the extract dried, evaporated, the residue crystallized from petroleum ether and recrystallized from ethyl acetate-hexane to give the 1-(2-piperidinoethyl)-3,4,5,5a,6,7-hexahydro-9-methoxy-2H-naphth[1,2d]azepin-2-one melting at 125°–128°. Its hydrochloride melts (after drying at 100°/0.01 mmHg) at 223°–225°.

The correspondingly obtained dimethylamino-base melts at 141°–143°.

EXAMPLE 5

The mixture of 4.7 g of 1-(2-oxopropyl)-9-methoxy-3-methyl-3,4,5,5a,6,7-hexahydro-2H-naphth[1,2-d]azepin-2-one, 8.88 ml of isopropylamine, 3.45 ml of 5 N methanolic hydrochloric acid, 1.02 g of sodium cyanoborohydride and 75 ml of methanol is stirred and refluxed overnight. An additional 1.02 g of sodium cyanoborohydride is added and refluxing is continued for another day. The mixture is cooled, acidified to pH=1 with concentrated hydrochloric acid, the methanol is evaporated and the solution washed with diethyl ether. It is rendered basic to pH=10-11 with 3 N aqueous sodium hydroxide, extracted with diethyl ether, the extract dried and evaporated. The residue is recrystallized from hexane, to yield the 1-(2-isopropylaminopropyl)-9-methoxy-3-methyl-3,4,5,5a,6,7-hexahydro-2H-naphth[1,2-d]azepin-2-one melting at 118°–120°.

The starting material is prepared as follows: The mixture of 20 g of 1-(2-oxopropyl)-3,4,5,5a,6,7-hexahydro-9-methoxy-2H-naphth[1,2-d]azepin-2-one, 37.5 ml of ethylene glycol and 0.95 g of boron trifluoride etherate in benzene is refluxed under a water trap for 6 hours. It is cooled and 10 g of sodium hydroxide in 140 ml of water are added rapidly and the mixture is extracted with chloroform. The extract is dried, evaporated and the residue is crystallized from diethyl ether, to yield the 1-(2-methyl-1,3-dioxolan-2-yl-methyl)-9-methoxy-3,4,5,5a,6,7-hexahydro-2H-naphth[1,2-d]azepin-2-one melting at 192°–194°.

To the solution of 10.1 g thereof in 98 ml of dimethylformamide, 1.86 g of a 57% oil dispersion of sodium hydride are added and the mixture is stirred at room temperature for 2 hours. The solution of 41.8 g of methyl iodide in 25 ml of dimethylformamide is added dropwise, the mixture stirred at room temperature overnight and added to 1 liter of ice water. It is extracted with diethyl ether, the extract dried, evaporated and the residue crystallized from ether-petroleum ether, to yield the 1-(2-methyl-1,3 -dioxolan-2-yl-methyl)-9-methoxy-3-methyl-3,4,5,5a,6,7-hexahydro-2H-naphth[1,2-d]azepin-2-one melting at 112°–115°.

The solution of 7.5 g thereof in 75 ml of 0.5 N hydrochloric acid and 75 ml of ethanol is stirred at room temperature for 24 hours and filtered. The residue is washed with water, to yield the 1-[2-oxopropyl]-9-methoxy-3-methyl-3,4,5,5a,6,7-hexahydro-2H-naphth[1,2-d]azepin-2-one melting at 190°–192°.

EXAMPLE 6

The solution of 0.84 g of 1-(2-oxopropyl)-9-methoxy-3-methyl-3,4,5,5a,6,7-hexahydro-2H-naphth[1,2-d]azepine hydrochloride, 1.28 ml of isopropylamine, 0.66 ml of 4.4 N methanolic hydrochloric acid and 0.17 g of sodium cyanoborohydride in 13 ml of methanol is refluxed overnight. Additional 0.085 g of sodium cyanoborohydride are added and the whole is again refluxed for 5 hours. The mixture is cooled, acidified to pH=1 with concentrated hydrochloric acid and the methanol evaporated. The aqueous solution is washed with diethyl ether, rendered basic to pH=10-11 with 3 N aqueous sodium hydroxide and extracted with diethyl ether. The ether extract is evaporated, the residue dissolved in acetone and 0.4 ml of 8 N ethanolic hydrochloric acid are added, to yield the 1-(2-isopropylaminopropyl)-9-methoxy-3-methyl-3,4,5,5 a,6,7-hexahydro-2H-naphth[1,2-d]azepine dihydrochloride melting at 257°–260° with decomposition.

The starting material is prepared as follows: 105 ml of a 1.1 M solution of alane-triethylamine in benzene are added dropwise to the solution of 31.2 g of 1-(2-methyl-1,3-dioxolan-2-yl-methyl)-9-methoxy-3-methyl-3,4,5,5a,6,7-hexahydro-2H-naphth-[1,2-d]azepin-2-one in 200 ml of anhydrous tetrahydrofuran at 0°. The mixture is stirred at 0° for 4 hours whereupon 44 ml of water are added slowly, followed by 88 ml of 3 N aqueous sodium hydroxide at 0°. The resulting mixture is extracted with diethyl ether, the extract dried and evaporated to give the 1-(2-methyl-1,3-dioxolan-2-yl-methyl)-9-methoxy-3-methyl-3,4,5,5a,6,7-hexahydro-2H-naphth[1,2-d]azepine.

The solution of 32 g thereof in 320 ml of ethanol and 320 ml of 0.5 N hydrochloric acid is stirred at room temperature for 20 hours. The ethanol is evaporated at room temperature, the aqueous solution washed with diethyl ether, rendered basic to pH=10-11 with 3 N aqueous sodium hydroxide and extracted with chloroform. The extract is washed with water, evaporated, the resulting oil dissolved in diethyl ether, the solution treated with 3.9 N ethanolic hydrochloric acid and the precipitate recrystallized from isopropanol-acetone, to yield the 1-(2-oxopropyl)-9-methoxy-3-methyl-3,4,5,5a,6,7-hexahydro-2H-naphth[1,2-d]azepin hydrochloride melting at 230°–232°.

EXAMPLE 7

5 ml of 1.1 M alane-triethylamine in benzene are added dropwise to the solution of 0.68 g of 1-(2-isopropylaminopropyl)-9-methoxy-3,4,5,5a,6,7-hexahydro-2H-naphth[1,2-d]azepin-2-one in 10 ml of anhydrous tetrahydrofuran and the mixture is refluxed for 5 hours. It is cooled in an ice bath and 2 ml of water, 2 ml of 3 N aqueous sodium hydroxide and 5 ml more of water are added in this order. The organic phase is separated, the aqueous portion extracted with chloroform and the combined extracts dried and evaporated. The residue is dissolved in acetone and the solution treated with 0.25 ml of 8 N ethanolic hydrochloric acid, to yield the 1-[2-(isopropylamino)-9-methoxy-3,4,5,5a,6,7-hexahydro-2H-naphth[1,2-d]azepine dihydrochloride melting at 273°–275°. Recrystallization from ethanol raises the melting point to 288°–290°.

EXAMPLE 8

To the stirred suspension of 4 g of 1-chloromethyl-3,4,5,5a,6,7-hexahydro-9-methoxy-2H-naphth[1,2-d]azepin-2-one in 80 ml of methylene chloride is added 8 ml of isopropylamine. The mixture is stirred at room temperature overnight, 80 ml of saturated aqueous sodium carbonate are added, the organic layer is separated, washed with water, dried and evaporated. The residue is crystallized from diethyl ether and recrystallized from ethyl acetate, to give the 1-isopropylaminomethyl-3,4,5,5a, 6,7-hexahydro-9-methoxy-2H-naphth[1,2-d]azepin-2-one melting at 212°–214°.

The starting material is prepared as follows: 36.4 ml of 2.5 M n-butyl lithium in hexane are added dropwise under nitrogen and at room temperature to the stirred suspension of 7.8 g of 1-methyl-9-methoxy-3,4,5,5a,6,7-hexahydro-2H-naphth[1,2-d]-azepin-2-one in 70 ml of anhydrous tetrahydrofuran. The mixture is stirred at room temperature for 45 minutes and cooled in a dry ice-acetone bath. The solution of 5.45 ml of dimethyl disulfide in 60 ml of tetrahydrofuran is added dropwise and the mixture stirred with said cooling for 2 hours. It is quenched by the slow addition of 150 ml of water, the mixture is extracted with chloroform, the extract is dried and evaporated. The residue is crystallized from diethyl ether and recrystallized from ethyl acetate, to give the 1-methylthiomethyl-3,4,5,5a,6,7-hexahydro9-methoxy-2H-naphth[1,2-d]azepin-2-one melting at 182°–184°.

To the ice-cooled, stirred suspension of 8.2 g thereof in 90 ml of methylene chloride, 4.58 ml of sulfuryl chloride are added dropwise and the mixture is stirred at room temperature for 3 hours. It is diluted with 50 ml of methylene chloride, washed several times with saturated aqueous sodium bicarbonate, dried and evaporated at room temperature. The residue is crystallized from diethyl ether, to yield the 1-chloromethyl-3,4,5,5a,6,7-hexahydro-9-methoxy-2H-naphth[1,2-d]azepin-2-one melting at 135°–138°.

EXAMPLE 9

The mixture of 7.2 g of 1-(2-oxopropyl)-8-methoxy-2,3,4,5,5a,6-hexahydro-indeno[1,2-d]azepin-2-one, 6.6 ml of 4.4 N ethanolic hydrochloric acid, 14.8 ml of piperidine, 1.7 g of sodium cyanoborohydride and 130 ml of methanol is refluxed for 24 hours while stirring. It is cooled, acidified to pH=1 with concentrated hydrochloric acid and the methanol evaporated. The residue is diluted with water, washed with diethyl ether, rendered basic to pH=10-11 with 3 N aqueous sodium hydroxide and extracted with chloroform. The extract is dried, evaporated and the residue crystallized from diethyl ether and recrystallized from aqueous ethanol to give the 1-(2-piperidinopropyl)-8-methoxy-2,3,4,5,5a,6-hexahydro-indeno[1,2-d]azepin-2-one melting at 184°–186°.

The starting material is prepared as follows: To the solution of 47.5 g of 2-piperidinomethyl-5-methoxy-1-indanone hydrochloride (m.p. 177°–180°) in 290 ml of water, 13.5 ml of concentrated hydrochloric acid are added, followed by the slow addition of the solution of 21 g of potassium cyanide in 160 ml of water, which is introduced below the surface of the liquid. The mixture is refluxed for 2½ hours, cooled, the resulting precipitate filtered off and dried, to yield the 2-cyanomethyl-5-methoxy-1-indanone, melting at 117°–120°.

The solution of 38 g thereof in 800 ml of ethanol is hydrogenated in the presence of the equivalent weight of Raney nickel a room temperature and atmospheric pressure until 2 mole equivalents of hydrogen are consumed. The mixture is filtered, evaporated and the residue dissolved in 6 N hydrochloric acid. The acidic solution is washed with diethyl ether, basified to pH=10 with 3 N aqueous sodium hydroxide and extracted with chloroform. The extract is evaporated and the solution of the residue in toluene is refluxed for two hours with continuous water removal.

To the refluxing solution (presumably containing 6-methoxy-2,3,3a,4-tetrahydro-indeno[1,2-d]pyrrole), 28 g of α-angelicalactone are added in 4 portions at hourly intervals. Refluxing is continued overnight, the resulting solution is cooled, filtered and the residue recrystallized from ethyl acetate, to yield the 1-(2-oxopropyl)-8-methoxy-2,3,4,5,5a,6-hexahydro-indeno[1,2-d]azepin-2-one melting at 196°–198°.

EXAMPLE 10

The solution of 7.5 g of the slow moving 1-(2-isopropylaminopropyl)-9-methoxy-3,4,5,5a,6,7-hexahydro-2H-naphth[1,2-d]azepin-2-one (Example 1) in 125 ml of methylene chloride is added slowly to 125 ml of a stirred 10 percent solution of boron tribromide in methylene chloride, precooled in a dry ice-acetone bath. The mixture is allowed to warm to room temperature slowly and is stirred overnight. It is cooled in an ice bath, 100 ml of water and 100 ml of 3 N aqueous sodium hydroxide are added and stirring is continued for one half hour. The basic aqueous solution is separated, washed with diethyl ether, neutralized to pH=8-9 with hydrochloric acid and allowed to stand overnight. The product, collected by filtration and subsequent extraction with chloroform, is suspended in 5 percent aqueous sodium bicarbonate and the suspension is stirred for 4 hours. The insoluble product is collected, dried and recrystallized from ethanol, to yield 1-(2-isopropylaminopropyl)-9-hydroxy-3,4,5,5a,6,7-hexahydro-2H-naphth[1,2-d]azepin-2-one as a single diastereoisomer, melting at 202°–204°.

EXAMPLE 11

The solution of 5 g of the slow moving 1-(2-isopropylaminopropyl)-9-methoxy-3,4,5,5a,6,7-hexahydro-2H-naphth[1,2-d]-azepin-2-one (Example 1) in 100 ml of glacial acetic acid is hydrogenated in the presence of 5 g of platinum oxide catalyst at room temperature and 3 atm. for 4 days. It is filtered, the filtrate evaporated and the residue dissolved in water. The solution is rendered basic to pH=10 with 3 N aqueous sodium hydroxide and extracted with chloroform. The extract is dried, evaporated, the resulting oil dissolved in acetone and treated with the stoichiometric amount of 8 N ethanolic hydrochloric acid, whereupon the 1-(2-isopropylaminopropyl)-9-methoxy-1,3,4,5,5a,6,7-11b-octahydro-2H-naphth[1,2-d]azepin-2-one hydrochloride crystallizes; it melts at 248°–250°.

Similar treatment of the fast moving 1-(2-isopropylaminopropyl)-9-methoxy-3,4,5,5a,6,7-hexahydro-2H-naphth[1,2-d]-azepin-2-one (RS-isomer), yields the corresponding fast moving octahydro compound, which is purified as the free base by crystallization from petroleum ether and recrystallization from ethyl acetate-hexane; it melts at 140°–142°.

EXAMPLE 12

24.4 ml of 37 percent aqueous formaldehyde are added to the stirred suspension of 10.3 g of slow moving 1-(2-isopropylaminopropyl)-9-methoxy-3,4,5,5a,6,7-hexahydro-2H-naphth[1,2-d]azepin-2-one (Example 1) in 15.7 ml of formic acid. The mixture is refluxed for 8 hours, evaporated and the residue suspended in water. The mixture is basified to pH=10-11 with 3 N aqueous sodium hydroxide and extracted with chloroform. The extract is dried, evaporated, and the residue crystallized from diethyl ether, to give the 1-[2-(N-isopropyl-N-methylamino)-propyl]-3-hydroxymethyl-9-methoxy-3,4,5,5a,6,7-hexahydro-2H-naphth[1,2-d]azepin-2-one melting at 158°–161°, (R,R-isomer).

The solution of 3.65 g thereof in the mixture of 9 ml of concentrated aqueous ammonium hydroxide, 80 ml of water and 70 ml of tetrahydrofuran is stirred at room temperature overnight. The tetrahydrofuran is removed by distillation and the resulting aqueous suspension extracted with chloroform. The extract is evaporated, the residue crystallized from petroleum ether and recrystallized from hexane, to yield the corresponding 3-unsubstituted compound melting at 150°–152°, (R,R-isomer).

EXAMPLE 13

13.3 ml of glacial acetic acid are added dropwise to an ice cooled mixture of 25 g of the slow moving 1-(2-isopropylaminopropyl)-9-methoxy-3,4,5,5a,6,7-hexahydro-2H-naphth[1,2-d]azepin-2-one hydrochloride, 53.1 ml of 37% formalin, 12.6 g of sodium cyanoborohydride and 266 ml of acetonitrile. The mixture is stirred at room temperature for one hour, acidified to pH=1 with concentrated hydrochloric acid and evaporated. The residue is diluted with water, the aqueous solution washed with diethylether, basified to pH=10-11 with 3 N aqueous sodium hydroxide and extracted with chloroform. The extract is dried, evaporated and the solution of the residue in a mixture of 65 ml concentrated aqueous ammonium hydroxide, 585 ml of water and 500 ml of tetrahydrofuran is stirred at room temperature overnight and filtered. The tetrahydrofuran is removed by distillation, the remaining aqueous suspension extracted with chloroform, the extract dried and evaporated. The residue is crystallized from cyclohexane, to give R,R-1-[2-(N-isopropyl-N-methylamino)-propyl]-9-methoxy-3,4,5,5a,6,7-hexahydro-2H-naphth[1,2-d]azepin-2-one melting at 145°–148°. Its hydrochloride melts at 261°–263°.

EXAMPLE 14

The mixture of 7.58 g of slow moving 1-(2-isopropylaminopropyl)-9-methoxy-3,4,5,5a,6,7-hexahydro-2H-naphth[1,2-d]azepin-2-one hydrochloride, 4.8 g of allyl bromide, 5.5 g of potassium carbonate and 100 ml of anhydrous ethanol is refluxed for 3 hours. The mixture is recharged with 2.4 g of allyl bromide and 2.75 g of potassium carbonate and refluxed overnight. It is evaporated, water is added to the residue and the mixture extracted with chloroform. The extract is evaporated, the residue crystallized from petroleum ether and recrystallized from ethyl acetate to yield the 1-[2-(N-isopropyl-N-allylamino)propyl]-9-methoxy-3,4,5,5a,6,7-hexahydro-2H-naphth[1,2-d]azepin-2-one, melting at 168°–170°.

EXAMPLE 15

4.09 ml of glacial acetic acid are added dropwise to the ice-cooled mixture of 7.7 g of slow moving 1-(2-isopropylaminopropyl)-9-methoxy-3,4,5,5a,6,7-hexahydro-2H-naphth[1,2-d]azepin-2-one . HCl, 11.4 ml of acetaldehyde, 3.89 g of NaCNBH$_3$ and 82 ml of acetonitrile. The mixture is stirred at room temperature for 2 hours, cooled, acidified to pH=1 with concentrated hydrochloric acid and evaporated. The residue is diluted with water, the solution washed with diethyl ether, basified to pH=10-11 with 3 N aqueous sodium hydroxide and extracted with chloroform. The extract is dried, evaporated, the residue crystallized from petroleum ether and recrystallized from hexane, to give the R,R-1-[2-(N-isopropyl-N-ethylamino)-propyl]-9-methoxy-3,4,5,5a,6,7-hexahydro-2H-naphth[1,2-d]azepin-2-one, melting at 150°–152°; its hydrochloride melts at 239°–241°.

EXAMPLE 16

To the solution of 5.0 g of the slow moving 1-(2-isopropylaminopropyl)-9-methoxy-3,4,5,5a,6,7-hexahydro-2H-naphth[1,2-d]azepin-2-one hydrochloride in 66 ml of anhydrous ethanol are added 3.64 g of anhydrous potassium carbonate and 3.14 ml of benzyl bromide. The mixture is refluxed for 3 hours while stirring and half of the original quantities of potassium carbonate and benzyl bromide are added. Refluxing is continued overnight and a second addition of the same reagents and refluxing for an additional day leads to complete benzylation. The mixture is evaporated, the residue diluted with water, extracted with chloroform and the extract dried and evaporated. The crude product is crystallized from petroleum ether and recrystallized from ethanol to give the 1-[2-(N-isopropyl-N-benzylamino)-propyl]-9-methoxy-3,4,5,5a,6,7-hexahydro-2H-naphth[1,2-d]azepin-2-one, melting at 205°–207°.

EXAMPLE 17

The solution of 5 g of the slow moving 1-(2-isopropylaminopropyl)-9-methoxy-3,4,5,5a,6,7-hexahydro-2H-naphth[1,2-d]azepin-2-one in 50 ml of acetic anhydride is refluxed for 3 hours and evaporated. The residue is dissolved in chloroform, the solution washed with saturated aqueous sodium bicarbonate, dried and evaporated. 6.3 g of the crude product are taken up in the solution of 63 g of liquid ammonia in 40 ml of methanol and the mixture is stirred in a pressure tube at room temperature for 3 hours. It is evaporated and the residue recrystallized from ethyl acetate, to yield the R,R-1-[2-(N-acetyl-N-isopropylamino)propyl]-9-methoxy-3,4,5,5a,6,7-hexahydro-2H-naphth[1,2-d]azepin-2-one, melting at 215°–217°.

Replacing the starting material with the fast moving R,S-racemate, the corresponding R,S-acetyl compound is obtained, melting at 204°–206°.

EXAMPLE 18

2.48 ml of 1.07 M alane-triethylamine in benzene are added dropwise to the stirred suspension of 0.77 g of RS-1-[2-(N-acetyl-N-isopropylamino)-propyl]-9-methoxy-3,4,5,5a,6,7-hexahydro-2H-naphth[1,2-d]azepin-2-one in 6 ml of tetrahydrofuran at 0°. The mixture is stirred at 0° for 3 hours and quenched by the slow addition of 3 ml of water, followed by 3 ml of 3 N aqueous sodium hydroxide while cooling. It is extracted with chloroform, the extract dried, evaporated, the residue crystallized from petroleum ether and recrystallized from ethanol-water, to give the RS-1-[2-(N-ethyl-N-isopropylamino)-propyl]-9-methoxy-3,4,5,5a,6,7-hexahydro-2H-naphth[1,2-d]azepin-2-one, melting at 163°–164°.

300 ml of benzene while stirring under nitrogen at 0°. The mixture is stirred at room temperature overnight, cooled with an ice bath and slowly combined with the solution of 17 g of sodium hydroxide in 250 ml of water while stirring. It is filtered, the filtrate washed with water, dried and evaporated. The residue is crystallized from diethyl ether and recrystallized from ethyl acetate, to yield the RS-1-(2-isopropyliminopropyl)-9-methoxy-3,4,5,5a,6,7-hexahydro-2H-naphth[1,2-d]azepin-2-one, melting at 162°–164°.

EXAMPLE 20

According to the methods illustrated by the previous examples, especially those listed in the Table below ("Ex."), the following compounds of Formula II are prepared from equivalent amounts of the corresponding starting materials: X=O Isomers ("IS") are denoted either by relative migration in thin layer chromatography; stationary phase is silica gel and moving phase is ethyl acetate-ethanol-aqueous ammonia (90:10:3), as slow (S) or fast (F) moving, or as mixtures (M) of both; or as being derived from a slow- or fast-moving starting material.

| No. | $R_0$ | $R_1$ | $R_2$ | $R_3$ | $R_4$ | $R_5$ | m | q | Am' | Salt | LS | Ex | m.p. C.° |
|---|---|---|---|---|---|---|---|---|---|---|---|---|---|
| 1 | H | H | H | H | H | $CH_3$ | 2 | 1 | $NHCH(CH_3)_2$ | HCl | S | 1 | 248–9 |
| 2 | H | H | H | H | H | " | 2 | 1 | " | " | F | 1 | 263–5 |
| 3 | H | H | OH | H | H | " | 2 | 1 | " | — | F | 10 | 209–1 |
| 4 | H | Cl | H | H | H | " | 2 | 1 | " | — | S | 1 | 178–0 |
| 5 | H | H | $OCH_3$ | H | H | " | 1 | 1 | " | HCl | M | 9 | 188–5 |
| 6 | H | H | H | $OCH_3$ | H | " | 2 | 1 | " | " | S | 1 | 265–6 |
| 7 | $OCH_3$ | H | H | " | H | " | 2 | 1 | " | — | M | 1 | 139–1 |
| 8 | H | $OCH_3$ | $OCH_3$ | H | H | " | 2 | 1 | " | — | S | 1 | 195–8 |
| 9 | H | H | H | H | H | " | 2 | 1 | $N(CH_3)_2$ | — | M | 1 | 149–0 |
| 10 | H | H | $OCH_3$ | H | H | H | 2 | 0 | " | — | — | 8 | 187–9 |
| 11 | H | H | " | H | H | H | 2 | 1 | " | — | — | 4 | 141–3 |
| 12 | H | H | " | H | H | $CH_3$ | 2 | 1 | " | — | F | 1 | 200–2 |
| 13 | H | H | " | H | $CH_2OH$ | " | 2 | 1 | $CH_3-NCH(CH_3)_2$ | — | F | 12 | 146–8 |
| 14 | H | H | " | H | H | " | 2 | 1 | " | — | F | 12 | 160–1 |
| 15 | H | H | " | H | H | " | 2 | 1 | $C_2H_5-NCH(CH_3)_2$ | — | F | 15 | 163–4 |
| 16 | H | H | " | H | H | " | 2 | 1 | $C_3H_7-NCH(CH_3)_2$ | — | S | 15 | 161–3 |
| 17 | H | H | " | H | H | " | 2 | 1 | $CH_3(CH_2)_3-NCH(CH_3)_2$ | — | S | 15 | 159–1 |
| 18 | H | H | " | H | H | " | 2 | 1 | $CH_3(CH_2)_6-NCH(CH_3)_2$ | — | S | 15 | 102–4 |
| 19 | H | H | " | H | H | " | 2 | 1 | $CH\equiv C-CH_2-NCH(CH_3)_2$ | — | S | 14 | 146–8 |
| 20 | H | H | " | H | H | H | 2 | 0 | $N(CH_2)_5$ | — | — | 8 | 214–6 |
| 21 | H | H | " | H | H | $CH_3$ | 2 | 1 | " | — | S | 1 | 162–4 |
| 22 | H | H | " | H | H | $CH_3$ | 2 | 1 | " | HCl | F | 1 | 254–5 |
| 23 | H | $OCH_3$ | H | H | H | " | 2 | 1 | " | " | F | 1 | 266–7 |
| 24 | H | H | $OCH_3$ | H | H | " | 2 | 1 | $N(CH_2)_4$ | — | S | 1 | 173–5 |
| 25 | H | H | " | H | H | " | 2 | 1 | morpholino | HCl | S | 1 | 255–7 |
| 26 | H | H | " | H | H | " | 2 | 1 | $CH_3-N-C_2H_5$ | " | S | 1 | 256–7 |

EXAMPLE 19

The solution of 1 g of 1-(2-isopropyliminopropyl)-9-methoxy-3,4,5,5a,6,7-hexahydro-2H-naphth[1,2-d]azepin-2-one in 50 ml of ethanol is hydrogenated at room temperature and atmospheric pressure for 2 hours in the presence of 0.1 g of platinum dioxide catalyst. The mixture is filtered, the filtrate evaporated and the residue crystallized from petroleum ether, to yield the 1-(2-isopropylaminopropyl)-9-methoxy-3,4,5,5a,6,7-hexahydro-2H-naphth[1,2-d]azepin-2-one as a mixture of the "slow" and "fast" moving isomers, melting at 118°–126°.

The starting material is prepared as follows: The solution of 11 ml of titanium tetrachloride in 100 ml of benzene is added dropwise to the mixture of 10 g of 1-(2-oxopropyl)-9-methoxy-3,4,5,5a,6,7-hexahydro-2H-naphth[1,2-d]azepin-2-one, 30 g of isopropylamine and Compound No. 26 may also be prepared as follows: 8.5 ml of glacial acetic acid are added to the solution of 8.9 g of N-methyl-ethylamine in 100 ml of acetonitrile, followed by 7.5 g of 1-(2-oxo-propyl)-9-methoxy-3,4,5,5a,6,7-hexahydro-2H-naphth[1,2-d]azepin-2-one and 1.7 g of sodium cyanoborohydride. The mixture is refluxed overnight, an additional 1.7 g of sodium cyanoborohydride is added and refluxing is continued for an additional day. The mixture is cooled, acidified to pH=1 with hydrochloric acid and evaporated. Water is added to the residue, the mixture is washed with diethyl ether, filtered and the aqueous filtrate basified to pH=10–11 with 3 N aqueous sodium hydroxide. It is extracted with chloroform, the extract dried, evaporated and the residue is dissolved in the minimum amount of ethanol. The solution is combined with 2.15 ml of 8 N ethanolic hydrochloric acid, the precipitate collected and recrystallized from ethanol, to yield the 1-[2-(N-ethyl-N-methylamino)-propyl]-9-methoxy-3,4,5,5a,6,7-hexahydro-2H-naphth[1,2-d]azepin-2-one hydrochloride, melting at 256°–257°.

The various new starting materials, used for said compounds Nos. 4, 7 and 8, are identified as follows:

(a) 2-cyanomethyl-1-tetralones: 7-chloro-derivative m.p. 86°–89°; 5,8-dimethoxy-derivative m.p. 118°–121°;

(b) 3,3a,4,5-tetrahydro-2H-benz [g] indoles: 8-chloro-derivative m.p. 119°–121°; 6,9-dimethoxy-derivative m.p. 75°–78°;

(c) 1-(2-oxopropyl)-3,4,5,5a,6,7-hexahydro-2H-naphth[1,2-d]azepin-2-ones: 10-chloro-derivative m.p. 242°–245°; 8,11-dimethoxy-derivative m.p. 183°–185°; 9,10-dimethoxy-derivative m.p. 220°–222°.

EXAMPLE 21

Preparation of 10,000 tablets each containing 100.0 mg of the active ingredient:

| Formula: | |
| --- | --- |
| R,R-1-[2-(N-ethyl-N-isopropylamino)-propyl]-3,4,5,5a,6,7-hexahydro-9-methoxy-2H-naphth[1,2-d]azepin-2-one hydrochloride | 1,000.00 g |
| Lactose | 2,535.00 g |
| Corn starch | 125.00 g |
| Polyethylene glycol 6,000 | 150.00 g |
| Talcum powder | 150.00 g |
| Magnesium stearate | 40.00 g |
| Purified water | q.s. |

Procedure:

All the powders are passed through a screen with openings of 0.6 mm. Then the drug substance, lactose, talcum, magnesium stearate and half of the starch are mixed in a suitable mixer. The other half of the starch is suspended in 65 ml of water and the suspension added to the boiling solution of the polyethylene glycol in 260 ml of water. The paste formed is added to the powders which are granulated, if necessary, with an additional amount of water. The granulate is dried overnight at 35°, broken on a screen with 1.2 mm openings and compressed into tablets using concave punches with 10.3 mm diameter, uppers bisected.

Preparation of 10,000 capsules each containing 50.0 mg of the active ingredient:

| Formula: | |
| --- | --- |
| R,R-1-(2-isopropylaminopropyl)-3,4,5,5a,6,7-hexahydro-9-methoxy-2H-naphth[1,2-d]azepin-2-one hydrochloride | 500.0 g |
| Lactose | 2,350.0 g |
| Talcum powder | 150.0 g |

All the powders are passed through a screen with openings of 0.6 mm. Then the drug substance is placed in a suitable mixer and mixed first with the talcum, then with the lactose until homogenous. No. 2 capsules are filled with 300 mg of the mixture using a capsule filling machine.

Analogously tablets and capsules are prepared from one of the other compounds illustrated by examples 1 to 20 or 22 to 26.

EXAMPLE 22

By replacing in Example 8 the isopropylamine with the equivalent amount of N-ethyl-isopropylamine, the 1-(N-ethyl-N-isopropylominomethyl)-9-methoxy-3,4,5,5a,6,7-hexahydro-2H-naphth[1,2-d]azepin-2-one is obtained, melting at 136°–138°.

Substituting in Example 10 the product of Example 1 with 8 g of that of Example 15, the R'R-1-[2-(N-ethyl-N-isopropylamino)-propyl]-9-hydroxy-3,4,5,5a,6,7-2H-naphth[1,2-d]azepin-2-one is obtained, melting at 208°–210°.

Finally, one may replace the allyl bromide in Example 14 with the equivalent amount of propargyl bromide, and the slow moving 1-(2-(N-isopropyl-N-propargylamino)-propyl-9-methoxy-3,4,5,5a,6,7-hexahydro-2H-naphth[1,2-d]azepin-2-one is obtained, melting at 146°–148°.

EXAMPLE 23

The mixture of 5 g of slow moving 1-(2-isopropylaminopropyl)-9-methoxy-3,4,5,5a,6,7-hexahydro-2H-naphth[1,2-d]azepin-2-one and 14.75 ml of liquified ethylene oxide in 100 ml of absolute ethanol is stirred in a sealed pressure tube at room temperature for two days. The reaction mixture is recharged with an additional 14.75 ml portion of ethylene oxide and stirred for four additional days at room temperature. It is evaporated, the residue slurried in diethyl ether, collected by filtration and recrystallized from ethyl acetate to yield the 1-[2-(N-isopropyl-N-2-hydroxyethylamino)-propyl]-9-methoxy-3,4,5,5a,6,7-hexahydro-2H-naphth[1,2-d]azepin-2-one, RR racemate melting at 147°–149°.

EXAMPLE 24

The solution of 2.72 g of allyl bromide in 100 ml of absolute ethanol is added to the mixture of 4 g of slow moving 1-[2-(N-isopropyl-N-ethylamino)-propyl]-9-hydroxy-3,4,5,5a,6,7-hexahydro-2H-naphth[1,2-d]azepinone, 3.1 g of anhydrous potassium carbonate and 100 ml of absolute ethanol. The mixture is refluxed for three hours and evaporated. The residue is suspended in 100 ml of water and the mixture is extracted with diethyl ether. The extract is washed with water, dried, evaporated and the residue crystallized from petroleum ether, to yield the 1-[2-(N-isopropyl-N-ethylamino)propyl]-9-allyloxy-3,4,5,5,a,6,7-hexahydro-2H-naphth[1,2-d]azepin-2-one, RR racemate melting at 87°–89°.

EXAMPLE 25

2.66 ml of glacial acetic acid are added dropwise to the ice-cooled mixture of 5.0 g of slow moving 1-(2-isopropylaminopropyl)-9-methoxy-3,4,5,5a,6,7-hexahydro-2H-naphth[1,2-d]azepin-2-one hydrochloride, 15.2 g of heptaldehyde, 2.52 g of sodium cyanoborohydride and 53 ml of acetonitrile. The mixture is stirred at room temperature for 2 hours, cooled, acidified to pH=1 with concentrated hydrochloric acid and evaporated to remove the acetonitrile. The residue is diluted with water, the solution washed with diethyl ether, basified to pH=10–11 with 3 N aqueous sodium hydroxide and extracted with chloroform. The extract is dried, evaporated and the residue crystallized from ethanol-water (5:2) to give the 1-[2-(N-isopropyl-N-heptylamino)-propyl]-9-methoxy-3,4,5,5a,6,7-hexahydro-2H- naphth[1,2-d]azepin-2-one, RR racemate melting at 102°–104°.

EXAMPLE 26

The solution of 2.2 g of 1-[2-(N-isopropyl-N-heptylamino)propyl]-9-methoxy-3,4,5,5a,6,7-hexahydro-2H-naphth[1,2-d]azepin-2-one, RR racemate in 18 ml of methylene chloride, precooled in a dry ice-acetone bath, is added to 31.3 ml of a similarly cooled 10% solution of boron tribromide in methylene chloride. The mixture is allowed to reach room temperature and is stirred at said temperature overnight. It is cooled in an ice bath, neutralized to pH=9 with 75 ml of saturated aqueous sodium carbonate and stirred at room temperature for 3.5 hours. The methylene chloride layer is separated, washed with water, dried and evaporated. The residue is suspended in diethyl ether, the crystallized material is collected and recrystallized from ethyl acetate to give the 1-[2-(N-isopropyl-N-heptylamino)-propyl]-9-hydroxy-3,4,5,5a,6,7-hexahydro-2H-naphth[1,2-d]azepin-2one, RR racemate melting at 144°–146°.

I claim:
1. A compound of the formula

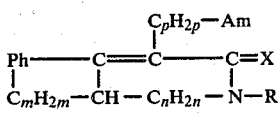

wherein pH is unsubstituted 1,2-phenylene, or 1,2-phenylene substituted by up to 3 members selected from lower alkyl, hydroxy, mercapto, lower alkoxy, lower alkylthio, lower alkenyloxy, halogeno and trifluoromethyl; $C_mH_{2m}$ is lower alkylene separating the adjacent atoms by one or two carbon atoms; $C_nH_{2n}$ is lower alkylene separating the adjacent atoms by two carbon atoms; p is an integer from 1 to 7; Am is amino, simple or mixed, mono- or di-lower (alkyl, alkenyl, alkynyl, hydroxyalkyl, 3 to 7 ring-membered cycloalkyl or H-Ph-alkyl)amino; 5 to 7 ring-membered cycloalkyl or H-ph-alkyl)amino; 5 to 7 ring-membered lower alkyleneimino, morpholino, thiamorpholino, piperazino or N-(lower alkyl or hydroxyalkyl)-piperazino; X represents oxo and R is hydrogen, lower alkyl or hydroxyalkyl; a lower alkanoyl- or 1,11b-dihydro-derivative, or a therapeutically acceptable acid addition salt thereof.

2. A compound as claimed in claim 1, in which formula Ph is 1,2-phenylene, (lower alkyl)-1,2-phenylene, (hydroxy)-1,2-phenylene, mono or di-(lower alkoxy)-1,2-phenylene, (halogeno)-1,2-phenylene or (trifluoromethyl)-1,2-phenylene; $C_mH_{2m}$ is methylene, ethylene or 1,2-propylene; $C_nH_{2n}$ is ethylene or 1,2-propylene, p is an integer from 1 to 7, Am is amino, lower (alkyl, alkenyl, alkynyl, hydroxyalkyl, 5 or 6 ring-membered cycloalkyl or phenyl-lower alkyl)amino, the N-lower alkyl-derivatives of said sec. amino groups; 5 to 7 ring-membered lower alkyleneimino, morpholino, thiamorpholino, piperazino or N-(lower alkyl or hydroxyalkyl)-piperazino; X represents oxo and R is hydrogen, lower alkyl or hydroxyalkyl; the lower alkanoyl derivatives of said compounds wherein Am is prim. or sec. amino, or both X and R are hydrogen; the 1,11b-dihydro-derivatives, or a therapeutically acceptable acid addition salt thereof.

3. A compound as claimed in claim 1, and corresponding to the formula

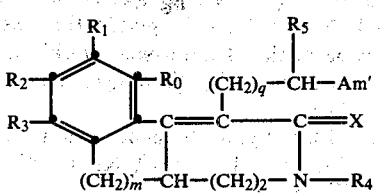

wherein each of $R_0$, $R_1$, $R_2$ and $R_3$ is hydrogen, or one thereof is alkyl with up to 4 carbon atoms, hydroxy, fluoro, chloro, bromo, or trifluoromethyl; or one or two thereof are alkoxy with up to 4 carbon atoms and the others are hydrogen, Am' is amino, lower (alkyl, alkenyl, alkynyl, hydroxyalkyl, 5 or 6 ring-membered cycloalkyl or benzyl)amino, the N-lower alkyl derivatives of said sec. amino groups, 5 to 7 ring-membered lower alkyleneimino, morpholino, thiamorpholino, piperazino or N-lower alkyl-piperazino; X represents oxo; each of $R_4$ and $R_5$ is hydrogen or alkyl with up to 4 carbon atoms; m is the integer 1 or 2 and q is 0 or 1; or a therapeutically acceptable acid addition salt thereof.

4. A compound as claimed in claim 3, in which formula each of $R_0$, $R_1$, $R_2$, and $R_3$ is hydrogen, or up to two of $R_0$, $R_1$, $R_2$ and $R_3$ are methoxy, or one thereof is methyl, hydroxy, fluoro, chloro or trifluoromethyl and the others are hydrogen; Am' is amino, (methyl, ethyl, n- or i-propyl, allyl, propargyl, 2-hydroxyethyl, cyclopentyl, cyclohexyl or benzyl)amino, or the N-(methyl, ethyl, n- or i-propyl, -butyl, -pentyl, -hexyl or -heptyl)-derivatives of said sec. amino groups, pyrrolidino, piperidino, morpholino or N-methylpiperazino; X is oxo; each of $R_4$ and $R_5$ is hydrogen or methyl; m is 2 and q is one; or a therapeutically acceptable acid addition salt thereof.

5. A compound as claimed in claim 3, in which formula each of $R_0$, $R_1$, $R_2$ and $R_3$ is hydrogen, or up to two thereof are methoxy and the others are hydrogen; $R_4$ is hydrogen; $R_5$ is methyl; Am' is (methyl, ethyl, n- or i-propyl, allyl or propargyl)amino, or the N-(methyl, ethyl, i-propyl or n-butyl)-derivative thereof, pyrrolidino, piperidino or morpholino; X is oxo, m is two and q is one; or a therapeutically acceptable acid addition salt thereof.

6. A compound as claimed in claim 3 and being the 1-(2-isopropylaminopropyl)-9-methoxy-3,4,5,5a,6,7-hexahydro-2H-naphth[1,2-d]azepin-2-one, or a therapeutically acceptable acid addition salt thereof.

7. A compound as claimed in claim 3 and being the 1-[2-(N-isopropyl-N-ethylamino)-propyl]-9-methoxy-3,4,5,5a,6,7-hexahydro-2H-naphth[1,2-d]azepin-2-one, or a therapeutically acceptable acid addition salt thereof.

8. A diuretic pharmaceutical composition comprising a diuretically effective amount of a compound as claimed in claim 1, together with a pharmaceutical excipient.

9. A method of traveling edematous conditions in mammals, which comprises administering to said mammals enterally or parenterally a composition as claimed in claim 8.

* * * * *